US006903130B1

(12) United States Patent
Lamberty et al.

(10) Patent No.: US 6,903,130 B1
(45) Date of Patent: Jun. 7, 2005

(54) PYRROLIDINEACETAMIDE DERIVATIVE ALONE OR IN COMBINATION FOR TREATMENT OF CNS DISORDERS

(75) Inventors: Yves Lamberty, Braine-le-Chateau (BE); Alain Matagne, Gerpinnes (BE); Henrik Klitgaard, Brussels (BE); Tony Waegemans, Leuven (BE)

(73) Assignee: UCB S.A., Brussels (BE)

( * ) Notice: Subject to any disclaimer, the term of this patent is extended or adjusted under 35 U.S.C. 154(b) by 0 days.

(21) Appl. No.: 10/148,347

(22) PCT Filed: Nov. 27, 2000

(86) PCT No.: PCT/EP00/11808

§ 371 (c)(1),
(2), (4) Date: Sep. 18, 2002

(87) PCT Pub. No.: WO01/39779

PCT Pub. Date: Jun. 7, 2001

(30) Foreign Application Priority Data

Dec. 1, 1999 (EP) .............................................. 99123803
Dec. 1, 1999 (EP) .............................................. 99124269

(51) Int. Cl.[7] .............................................. A61K 31/40
(52) U.S. Cl. ...................................... 514/423; 514/922
(58) Field of Search ................................ 514/423, 922, 514/220, 408, 183, 359, 740, 903

(56) References Cited

U.S. PATENT DOCUMENTS

| 4,696,943 A | 9/1987 | Gobert et al. |
| 5,998,380 A | 12/1999 | Ehrenberg et al. |
| 6,195,601 B1 * | 2/2001 | Spillner et al. ............... 701/41 |
| 6,495,601 B1 | 12/2002 | Hochman |

FOREIGN PATENT DOCUMENTS

| EP | 0162036 | 11/1985 |
| EP | 0 408 782 A1 | 1/1991 |
| EP | 0408782 | 1/1991 |
| WO | WO 99/31075 | 6/1999 |
| WO | WO 99/37296 | 7/1999 |

OTHER PUBLICATIONS

Fraser, et al., Effects of Anti–epileptic Drugs in Glutamine Synthetase Activity in Mouse Brain, British Journal of Pharmacology Apr., 1999, vol. 126, pp. 1634–1638.*
J. Prous, et al.; "Levetiracetam"*Drugs of the Future*, ES, Barcelona, vol. 19, No. 2, 1994, pp. 111–113.
Wilson, et al; "New Antiepileptic Drugs"; *Balliere's Clinical Neurology*, London, GB, vol. 5, No. 4, Dec. 1996, pp. 723–747.
H.G. Wiesser; "Treatment of epilepsies: current situation"; Schweizerische Rundschau for Medizin (PRAXIS), vol. 85, No. 4 (1996), pp. 74–79. (Translation included).
American Psychiatric Association; American Psychiatric Association Releases a Treatment Guieline for Bipolar Disease; American Family Physician, vol. 51, No. 6, 1995, pp. 1605–1609.
Post, Robert; "Comparative Pharmacology of Bipolar Disorder and Schizophrenia"; *Schizophrenia Research*; vol. 39, No. 2, Sep. 29, 1999, pp. 153–158.
Patsalos, P.N.; "Pharmacokinetic profile of levetiracetam; toward ideal characteristics"; *Pharmocology & Theraeputics*, vol. 85 (2000); pp. 77–85.
M. Bialer, et al; "Progress report on new antiepileptic drugs: a sunmary of the Third Eilat Conference"; *Epilepsy Research*; vol. 25 (1996); pp. 229–319.
Marcotte, D.; Use of topirmate, a new anti–epileptic as a mood stabilizer; *Journal of Affective Disorders*; vol. 50 (1998), pp. 245–251.

* cited by examiner

Primary Examiner—Frederick F. Krass
(74) Attorney, Agent, or Firm—McDonnell Boehnen Hulbert & Berghoff LLP

(57) ABSTRACT

A use of (S)-(–)-α-ethyl-2-oxo-1-pyrrolidineacetamide for the manufacture of a medicament for treatment of particular disease and new pharmaceutical compositions comprising (S)-(–)-α-ethyl-2-oxo-1-pyrrolidineacetamide.

5 Claims, No Drawings

PYRROLIDINEACETAMIDE DERIVATIVE ALONE OR IN COMBINATION FOR TREATMENT OF CNS DISORDERS

This application is a 371 of PCT/EP00/11808, filed Nov. 27, 2000.

The present invention relates to the use of (S)-(−)-α-ethyl-2-oxo-1-pyrrolidineacetamide for the preparation of drugs for the curative and/or prophylactic treatment of bipolar disorders, migraine, chronic or neuropathic pain and to pharmaceutical compositions comprising (S)-(−)-α-ethyl-2-oxo-1-pyrrolidineacetamide and at least one compound inducing neural inhibition mediated by $GABA_A$ receptors.

The (S)-(−)α-ethyl-2-oxo-1-pyrrolidineacetamide. of the formula:

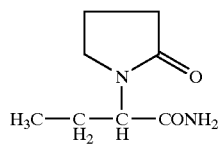

(1)

is also known and hereinafter referred to as levetiracetam [International Nonproprietary Name].

The use of levetiracetam, as a protective agent for the treatment and prevention of hypoxic and ischaemic type aggressions of the central nervous system (CNS) is described in European patent EP-B-0 162 036. The compound can also be employed in the treatment of epilepsy, a therapeutic indication for which it has been demonstrated that its dextrorotatory enantiomer, (R)-(−)-α-ethyl-2-oxo-1-pyrrolidine-acetamide, is completely devoid of activity (A. J. GOWER et al., Eur. J. Pharmacol., 222, (1992), 193–203). This latter compound has also been described in European patent EP-B-0 645 139, for the treatment of anxiety.

EP-B-0 162 036 cited above also describes methods for preparing levetiracetam which require the synthesis of a starting reactant obtained by resolution of the corresponding racemate. British patent GB 2 225 322, describes a method for preparing levetiracetam using a natural amino acid which already has the desired stereochemical configuration as the starting material.

It has now surprisingly been found that levetiracetam possesses therapeutic properties which render it particularly useful in the treatment and prophylaxis of bipolar disorders, mania, migraine and chronic or neuropathic pain. These activities are not observed in the dextrorotatory enantiomer, (R)-(+)-α-ethyl-2-oxo-1-pyrrolidineacetamide.

The present invention thus concerns the use of levetiracetam for the preparation of drugs for the treatment of bipolar disorders, mania, migraine and chronic or neuropathic pain.

The present invention also concerns a method for treating migraine, bipolar disorders, mania and chronic or neuropathic pain, comprising administering a therapeutic dose of levetiracetam to a patient in need of such treatment.

The term "treatment" as used herein means curative treatment and prophylactic treatment.

The term "curative" as used herein means efficacy in treating ongoing episodes (e.g., like manic phases or depressive phases in bipolar disorders).

The term "prophylactic" means the prevention of the onset or recurrence of manic/depressive, migraine or neuropathic pain episodes.

The term "migraine" as used herein means a disorder characterised by recurrent attacks of headache that vary widely in intensity, frequency, and duration. The headaches are commonly unilateral and are frequently associated with anorexia, nausea, vomiting, phonophobia, and/or photophobia. In some cases they are preceded by, or associated with, neurologic and mood disturbances. Migraine headache may last from 4 hours to about 72 hours. The International Headache Society [IHS, 1988] classifies migraine with aura (classical migraine) and migraine without aura (common migraine) as the major types of migraine. Migraine with aura consists of a headache phase preceded by characteristic visual, sensory, speech, or motor symptoms. In the absence of such symptoms, the headache is called migraine without aura.

One-year prevalence figures are primarily dependent on age and sex (Ferrari M D. "*Migraine*" The Lancet (1998); 351: 1043–1051—Sheffield R E. "*Migraine prevalence: a literature review*" Headache (1998); 38: 595–601).

Ten percent of the general population (6% of males and 15% of females) are active migraine sufferers. Prevalence peaks around 35 to 50 years of age in women and 25 to 35 years of age in men. Within the 10 to 19 years age group, there is a sharp increase in prevalence with age, with a peak around 14–16 years. Before puberty there is an equal prevalence between males and females. Among adults, the ratio of women to men is approximately 2.5:1. One-year prevalence rates for migraine without aura are 1.5 to 7 times higher than migraine with aura.

Migraine treatments can be divided into four types: general measures, abortive therapy, pain relief measures, and prophylactic treatment (Silberstein S D. "*Preventive treatment of migraine: an overview*" Cephalalgia (1997); vol. 17 p 67–72—Diamond S, Diamond M L. "*Contemporary diagnosis and management of headache and migraine*" (1998); First Edition. Handbooks in Health Care Co., Newtown, Pa., USA.

Diener H C, Kaube H, Limmroth V. "*A practical guide to the management and prevention of migraine*" Drugs (1998); vol. 56 (5): p811–824).

General measures may be a regular sleep schedule, regular meal schedule, dietary measures, etc. There are a variety of agents that may be used as abortive treatments, ranging from the simple analgesics such as acetyl salicylic acid, non-steroidal anti-inflammatory drugs (NSAIDs), ergot compounds, antiemetics, to the most recently developed serotonin (5-HT) agonists (triptan compounds).

Pain relief measures may include NSAIDs, narcotic analgesics, or rescue therapy. As for acute treatments there is a variety of medications that are used in the prophylaxis of migraine. Prophylactic treatment is usually given daily for months or years. It should be considered for patients who have two or more migraine attacks per month. Beta-adrenoceptor blockers—primarily propranolol—have been recognized for their efficacy in migraine prevention. Equally efficacious is the antiepileptic drug divalproex sodium. Other compounds are tricyclic antidepressants (amitriptyline), calcium channel blockers (nifedipine, flunarizine, verapamil), NSAIDs (ketoprofen, naproxen), riboflavin (vitamin B2), and 5-HT antagonists.

Traditional theories of migraine pathogenesis are the vasogenic theory and the neurogenic theory. Neither of these theories completely explains all of the clinical phenomena observed during a migraine attack.

Current views on migraine pathophysiology take into account both neurological and vascular events in the initiation of an attack. Endogenous neurophysiologic events activate trigeminovascular fibers in the brainstem, with subsequent perivascular release of powerful vasoactive neuropeptides. In animal experiments these neuropeptides promote a neurogenic inflammation response, consisting of vasodilatation and dural plasma extravasation. Cortical spreading depression (CSD) has been described as slowly spreading waves of inhibition of cortical neurons that is associated with the clinical symptoms of aura. Experimental CSD can activate the trigemino-vascular system in the brainstem, providing a possible link between aura and headache mechanisms.

There is some evidence that 5-HT acts as a neurotransmitter and humoral mediator in the neural and vascular components of the migraine headache.

Migraine patients have a systemic disturbance of the 5-HT metabolism.

It is theorized that persons prone to migraine have a reduced threshold for neuronal excitability, possibly due to diminished activity of the inhibitory neurotransmitter gamma-aminobutyric acid (GABA). GABA normally reduces the cellular effects of the neurotransmitter serotonin (5-HT) and glutamate, both of which appear to be involved in migraine attacks.

Divalproex sodium is a stable co-ordination compound comprising sodium valproate and valproic acid in a 1:1 molar relationship. Disordered GABA metabolism has been reported in migraine patients and changes in cerebrospinal GABA levels were found during migraine episodes. Divalproex sodium is thought to elevate brain levels of gamma-aminobutyric acid (GABA) by decreasing its degradation. The increased activity of GABAergic systems may influence the migraine generation directly or indirectly through a number of mechanisms. Potential indirect mechanisms include decreasing the firing rate of the serotonergic neurons in the-dorsal raphe nucleus.

The term "valproate" as used herein includes valproic acid and the derivatives such as valpromide, valproate pivoxil, magnesium valproate, divalproex sodium, sodium valproate and semi-sodium valproate.

Valproate has been reported to raise endogenous brain levels of enkephalin, which plays a determinant role in analgesia.

It has been postulated that valproate decreases levels of excitatory amino acids in the brain, interfering with CSD (Mathew NT and col. *"Migraine prophylaxis with divalproex"* Arch. Neurol. (1995); vol.52: p 281–286–Welch K M, D'Andrea G, Tepley N, Barkley G, Ramadan N M. *"The concept of migraine as a state of central neuronal hyperexcitability"* Neurol. Clin. (1990); vol.8. p 817–8281.

The most common side effects reported with valproate are nausea, vomiting, indigestion, asthenia, somnolence, dizziness, tremor, weight gain, and alopecia. Because most side effects are dose related, patient and physician should aim for the lowest possible therapeutic dose.

Valproate has a known risk of hepatic failure, particularly in young children. Liver function tests need to be performed at regular intervals. Valproate has been reported to produce teratogenic effects such as neural tube defects.

Nevertheless, the prevention of a migraine attack is preferable over suppression of an attack, because prophylactic treatment allows the patient greater freedom from the disease. This is especially true in more severe cases where patients have a higher frequency of attacks. The ultimate goal in all cases is complete freedom from any further attack, managed through continuing prophylactic treatment. Up to now, such a goal has only been achieved with valproate, but at a serious price of side effects as mentioned above and contra-indications (e.g., interactions with other medications and particularly potential for congenital malformations).

There is a genuine need to develop other alternatives and to provide a compound with a therapeutic margin that is more appropriate to the treatment and more particularly for the prophylactic treatment of this pathology.

To demonstrate that levetiracetam is particularly suitable for the treatment of migraine, with good therapeutic margin, clinical trials are be carried out in a manner known to the skilled person.

Such an activity is particularly unexpected due to the fact that levetiracetam is devoid of direct effects on the GABA system (H. Klitgaard and col., *"Evidence for a unique profile of levetiracetam in rodent models of seizures and epilepsy"* European Journal of Pharmacology (1998); vol. 353, p. 191–206). Potentiation of GABAergic inhibition has been proposed but extensive in vitro experiments have not revealed any significant displacement of ligands specific for 55 different binding sites including different receptor systems, reuptake sites, second messenger systems and channel proteins (M. Noyer and col. *"The novel antiepiieptic drug levetiracetam (ucb L059) appears to act via a specific binding site in CNS membranes"* European Journal of Pharmacology (1995), vol. 286, p 137–146). Furthermore, levetiracetam did not modulate chloride fluxes induced by muscimol. Finally, a lack of effect on GABA levels and the enzymatic activities of GABA transaminase and glutamic decarboxylase was reported from a neurochemical study on mouse brain (G. J. Sills and col. *"Neurochemical studies with the novel anticonvulsant levetiracetam in mouse brain"*; European Journal of Pharmacology; (1997) vol. 325 p 35–40).

Valproate is moreover the only antiepileptic drug that has been approved for its efficacy in the prophylactic treatment of migraine headache, thus, it was therefore no reason to expect that the antiepileptic drug levetiracetam with a different, as yet unknown, mode of action would also be particularly suitable for the treatment of migraine.

For all these reasons, the treatment or prophylactic treatment with levetiracetam is expected to combine beneficial effects in reduction of attacks, and improvements in quality of life and daily functioning.

The term "bipolar disorders" as used herein is defined below.

Bipolar disorders are classified as Mood Disorders according to the Diagnostic and Statistical Manual of Mental Disorders, 4th edition (Diagnostic and Statistical Manual of Mental Disorders (DSM-IV TM), American Psychiatry Association, Washington, D.C., 1994). Bipolar disorders are generally characterised by spontaneously triggered repeated (i.e. at least two) episodes in which the patient's hyperexcitability, activity and mood are significantly disturbed, this disturbance consisting on some occasions of an elevation of mood and increased energy and activity (mania or hypomania), and in other occasions a lowering of mood and decreased energy and activity (depression).

Bipolar disorders are separated into four main categories in the DSM-IV (bipolar I disorder, bipolar II disorder, cyclothymia, and bipolar disorders not otherwise specified).

The essential feature of bipolar I disorder is a clinical course that is characterized by one or more manic episodes alternated with one or more major depressive episodes.

The essential feature of bipolar II disorders is a clinical course that is characterized by one or more major depressive episodes accompanied by at least one hypomanic episode. No full manic or mixed episodes are present.

Cyclothymia is characterized by numerous periods of hypomanic symptoms that do not meet criteria for a manic episode and periods of depressive symptoms that do not meet symptom or duration criteria for a major depressive episode.

Bipolar disorders not otherwise specified may be made in addition to the diagnosis of schizophrenia, delusional disorders, or psychotic disorder not otherwise specified. If there is a very rapid alternation (over days) between manic symptoms and depressive symptoms (e.g., several days of purely manic symptoms followed by several days of purely depressive symptoms) that do not meet minimal duration criteria for a manic episode or major depressive episode, the diagnosis is bipolar disorders not otherwise specified.

By manic episode is meant a distinct period during which there is an abnormally and persistently elevated, expansive, or irritable mood with signs of pressured speech and psychomotor agitation.

By hypomania, is meant a less extreme manic episode, with lower grade of severity.

By major depressive episode, is meant a period of at least 2 weeks during which there is either depressed mood or the loss of interest or pleasure in nearly all activities with signs of impaired concentration and psychomotor retardation.

By mixed episode, is meant a period of time (lasting at least I week) in which the criteria are met both for a manic episode and for a major depressive episode nearly every day.

For a number of decades, the treatment of mania and manic recurrences in bipolar disorders has essentially been based on the use of lithium salts ($Li^+$). In recent years, the incomplete protection and tolerance furnished by long-term use of $Li^+$ for bipolar disorders has led to alternative treatments being considered. Clinical studies indicate that during the acute phase of bipolar disorder, up to 40% of patients do not satisfactorily respond to lithium treatment (Gustavo A. et al., *Anticonvulsants for treatment of manic depression*; Current Drug Therapy, vol. 56, No 8, 1989).

A number of safety problems linked to long-term use of lithium have been observed. Thus chronic interstitial nephropathy, polyuria, diabetes insipidus or nephrogenic diabetes insipidus occur in 25% of subjects treated over a period of more than two years. Further, normal use of lithium frequently induces dysarthria, trembling, ataxia, hypothyroidism (30% of subjects in the first two years) and impotence.

One of the most common alternative treatments is the use of an anticonvulsant, valproate, which has been shown to have an antimanic activity and is also capable of having a mood stabilizing activity. However, the results obtained are not yet satisfactory, and moreover valproate readily induces a variety of side effects. The usual side effects of valproate relate to the gastro-intestinal tract, such as nausea, vomiting, anorexia and diarrhea, as described in the preceding paragraph.

Pharmacological tests have demonstrated that in therapeutically active doses, valproate induces significant hyperactivity when given to a healthy control rodent. The prophylactic use of valproate in patients could therefore induce an effect contrary to the desired effect and/or produce a slight hyperactivity after each administration of a tablet. Similarly, during active treatment, valproate is capable of maintaining a hyperactive effect although the manic phase has passed. Finally, this study has demonstrated the difficulty of adapting the useful dose of lithium or valproate to the subject. Thus for these two compounds, a slight overdose tends to reduce rodent activity to below the level of the controls.

There is a genuine need to develop other alternatives to lithium or to valproate to avoid their numerous side effects and to provide a compound with a therapeutic margin, which is more appropriate to the treatment of this pathology.

Surprisingly it has been found that levetiracetam, in addition to its antimanic activity, only induces a very slight hyperactivity in control rats with no sign of mania. Levetiracetam would thus be particularly suitable for the treatment of mania.

A further unexpected advantage of levetiracetam is the provision of normalization to the level of the activity of the control, while valproate or lithium tend to go beyond this.

Thus in the case of valproate and lithium, too high a dose of these compounds could result in underactivity with respect to the normal state of the patient, which should be avoided.

Levetiracetam thus has a certain advantage, as it enables the practitioner to adapt the doses to the patient more easily, without risking inducing side effects of hypoactivity due to overdosing.

Similarly, the consequences of abusive intake of tablets by the patient would be minimized.

Finally, in the therapeutic doses used, levetiracetam also has the advantage of being far removed from doses at which it is capable of inducing side effects while compounds such as valproate or carbamazepine have a much reduced margin of safety (A. J. Gower et al., Eur. J. Pharmacol., 22, p 193–203 (1992)—W. Löscher and D. Hönack, Eur. J. Pharmacol.,232, p 147–158 (1993)—H. Klitgaard, A. Matagne, J. Gobert, E. Wülfert, Eur. J. Pharmacol.,353, p 191–206 (1998)).

This unforeseeable range of properties means that the use of levetiracetam is of particular interest for the manufacture of a medicament for the treatment of bipolar disorders. This compound has a safety margin in use which has never been achieved for this therapeutic category.

The term "chronic pain" as used herein is gradually being recognised as a disease process distinct from acute pain. Conventionally defined as pain that persists beyond the normal time of healing, pain can also be considered chronic at the point when the individual realises that the pain is going to be a persistent part of their lives for the foreseeable future. It is likely that a majority of chronic pain syndromes involves a neuropathic component, which is usually harder to treat than acute somatic pain.

The best examples of predominantly neuropathic pain syndromes are diabetic peripheral neuropathy and post herpetic neuralgia. A primarily somatic chronic pain syndrome is exemplified by patients with rheumatoid arthritis or other rheumatologic diseases. On the other hand, the most common chronic pain syndrome involving back injury related pain often involves multiple organ systems. The other major cause of chronic pain is cancer, which is known for its ability to cross tissue boundaries and damage or compress a variety of organ systems. Therefore, most back injury and cancer patients have pain related to both somatic and neuropathic mechanisms (H. C. Hansen, MD "*Treatment of chronic Pain With Antiepileptic Drugs: A New Era*" South Medical Journal—Southern Medical Association (1999) 92(7) p 642–649).

The term "neuropathic pain" as used herein, is a pain initiated by a pathological change in a nerve which signals the presence of a noxious stimulus when no such recognisable stimulus exists, giving rise to a false sensation of pain. In other words, it appears that the pain system has been turned on and cannot turn itself off.

It may be related to peripheral or central (spinal or brain) nerve lesions or dysfunction in the nervous system. Neuropathic pain can manifest as a result of conditions such as, nerve injury (e.g. surgery, accident, amputation), trauma affecting the limb (with or without obvious nerve lesions), diseases affecting the nervous system, infarct related to the nervous system, abnormal nerve function, spinal and radicular pain disorders.

By nerve injury, is meant conditions such as, phantom pain (pain referred to the amputated limb), stump pain (pain at the amputation site), phantom limb (non-painful sensations referred to the amputated limb), post-operative pain, thalamic pain syndrome (central post-stroke pain). By trauma affecting the limb, is meant conditions such as, reflex symptomatic dystrophy, Causalgia. By diseases affecting the nervous system, is meant conditions such as, diabetic neuropathy and other neuropathies, trigeminal neuralgia (TN), postherpetic neuralgia (PHN), multiple sclerosis, AIDS-related neuropathy, cancer-related neuropathy (neuropathy secondary to chemotherapy) (S. Troel, M. D. Jensen "*Mechanisms of Neuropathic Pain*" Pain 1996—An updated review, IASP Press SEATTLE (1996), p 77–86).

Chronic and/or neuropathic pains, remain the pain syndromes which are the most difficult to treat and there is a genuine need to develop novel active ingredients.

For almost thirty years, very little progress has been made in the drug treatment of chronic pain and neuropathic pain and this remains restricted to the use of antidepressants, Nonsteroidal Anti-inflammatory drugs, local anesthetics, and anticonvulsants.

A number of anticonvulsants, such as valproate or carbamazepine, possess activity in the treatment of these pain conditions, but others such as pentobarbital are ineffective (H. L. Fields et al., Excitability Blockers, p93–116—H. C. Hansen, MD "*Treatment of chronic Pain With Antiepileptic Drugs: A New Era*" South Medical Journal—Southern Medical Association (1999) 92(7) p 642–649).

Considerable precautions must be taken when using carbamazepine, which is a first line treatment, since the difference between the therapeutic dose and the dose inducing side effects is extremely small. Further, the posology inducing these effects varies depending on the patient. Thus the practitioner must be extremely vigilant when adjusting the doses to each individual treated. Side effects can include sedation, ataxia, dizziness, blurred vision, also nausea and vomiting. Further, about 10% of patients exhibit mild leukopenia (H. L. Fields et al., Excitability Blockers p 93–116).

Carbamazepine, which is the molecule in the antiepileptic category, which acts as a reference for pharmacological studies in the field of chronic or neuropathic pain, has a distinct activity in inhibiting artificially induced pain or hyperalgesia. However, pharmacological studies have confirmed that the dose-activity curve does not only reverse the pain to the control threshold (reversal of hyperalgesia), but it goes beyond that and induces partial desensitization in treated subjects (alteration of normal threshold). Thus in the doses used therapeutically, an antinociceptive effect is observed and the animal no longer feels pain which it would feel in its normal state. Such desensitization can be particularly awkward as regards no-risk use by the patient. Thus if a patient who wanted to reduce chronic or neuropathic pain took too high a dose of carbamazepine, he would be exposed to partial desensitization. Thus with his sensitivity threshold being higher than normal, he would be much less receptive to any external aggressions such as heat, chafing or the like, and thus would risk injuring himself or burning himself.

Pharmacological studies have revealed that levetiracetam behaves in an unexpected manner in the treatment of chronic or neuropathic pain. In contrast to carbamazepine, this molecule normalizes the dose/activity curve to the control pain threshold (i.e. response before induction of diabetes). Thus the use of levetiracetam has a very much higher safety margin of risk in the event of an overdose.

Further, in the therapeutic doses used, levetiracetam also has the advantage of being far removed from doses at which it is capable of inducing secondary effects while compounds such as carbamazepine have a greatly reduced safety margin.

This unexpected range of properties means that the use of levetiracetam is of particular importance for the manufacture of a medicament for treatment of chronic and/or neuropathic pain disorders.

The present invention requires administration of an effective dose of levetiracetam for the treatment of bipolar disorders, migraine and chronic or neuropathic pains. The dose required in accordance with the invention should be sufficiently high to permit the relief of bipolar disorders, migraine and chronic or neuropathic pains. Pharmaceutical compositions comprising levetiracetam can, for example, be administered orally or parenterally, e.g. intravenously, intramuscularly or subcutaneously or intrathecally.

Thus, the present invention concerns also a pharmaceutical composition for the treatment of bipolar disorders, mania, migraine and chronic or neuropathic pain comprising a therapeutically effective amount of levetiracetam and a pharmaceutically acceptable carrier.

Pharmaceutical compositions which can be used for oral administration can be solids or liquids and can, for example, be in the form of tablets, pills, dragees, gelatin capsules, solutions, syrups, and the like.

To this end, levetiracetam can be used mixed with an inert diluent or a non-toxic pharmaceutically acceptable vehicle such as starch or lactose, for example. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate. They also comprise compositions which can release the active ingredient in a controlled manner. Pharmaceutical compositions which can be used for parenteral administration are in the pharmaceutical forms which are known for this mode of administration and are in the form of aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiologic saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The daily dosage of active ingredient administered to the patient, can fall within a wide range of concentrations and depends on a variety of factors such as the patient's sex, age, weight and medical condition, as well as on the method of administration. Thus the quantity of active ingredient in compositions for oral administration is at least 0.5% by weight and can be up to 80% by weight with respect to the composition weight.

Clinical studies on healthy volunteers showed that levetiracetam is well tolerated at single dose (up to 5,000 g) and repeated doses 1500 mg/day for 14 days). Preliminary data from tolerability studies suggest good tolerability in epileptic patients of doses up to 4000 mg/day.

For the preferred oral compositions, the dosage unit is in the range 50 to 3000 milligrams (mg) and more preferably in the range 250 to 1500 mg of levetiracetam.

In compositions for parenteral administration, the quantity of levetiracetam present is at least 0.5% by weight and can be up to 33% by weight with respect to the composition weight. For the preferred parenteral compositions, the dosage unit is in the range 1 mg to 400 mg of levetiracetam.

The daily dose can fall within a wide range of dosage units of levetiracetam, and is generally in the range 5 to 70 mg/kilogram (kg). However, it should be understood that the specific doses can be adapted to particular cases depending on the individual requirements, at the physician's discretion.

Levetiracetam can be employed alone or combined with at least one other pharmaceutically active ingredient for use in these pathologies. Non-limiting examples or these compounds which can be cited for use in combination with levetiracetam are antivirals, antispastics (i.e.: baclofen), antiemetics, antimanic mood stabilizing agents, analgesics (i.e.: aspirin, ibuprofen, paracetamol), narcotic analgesics, topical anesthetics, opioid analgesics, lithium salts, antidepressants (i.e.: mianserin, fluoxetine, trazodone), tricyclic antidepressants (i.e.: imipramine, desipramine), anticonvulsants (i.e.: valproate, carbamazepine, phenytoin . . . ), antipsychotics (i.e.: risperidone, haloperidol), neuroleptics, benzodiazepines (i.e.: diazepam, clonazepam), phenothiazines (i.e.: chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives.

In particular, it has been discovered that levetiracetam potentiates the activity of compounds inducing neural inhibition mediated by $GABA_A$ receptors without exacerbating related side effects. As a result of this unexpected pharmacological property, patients obtaining control of their symptoms at the expense of marked adverse effects during monotherapy treatment with these compounds may obtain a significant improvement in their treatment outcome by combined dosing with a minor dose in combination with levetiracetam.

Thus, the present invention also relates to the unexpected fact that levetiracetam, known as an antiepileptic compound, is an effective potentiating agent of the anticonvulsant, and the anti-manic activity of valproate, clonazepam, chlordiazepoxide, phenobarbital and pharmaceutically acceptable salts thereof.

Examples of compounds inducing neural inhibition mediated by the $GABA_A$ receptors, we understand the following compounds: benzodiazepines, barbiturates, steroids, and anticonvulsants such as valproate, viagabatrine, tiagabine, or pharmaceutical acceptable salts thereof.

Benzodiazepines include the 1,4 benzodiazepines, such as diazepam and clonazepam, and the 1,5 benzodiazepines, such as clobazam. Preferred compound is clonazepam.

Barbiturates include phenobarbital and pentobarbital. Preferred compound is phenobarbital.

Preferred anticonvulsants include valproic acid, valpromide, valproate pivoxil, sodium valproate, semi-sodium valproate, divalproex, clonazepam, phenobarbital, vigabatrine, tiagabine.

Preferred compounds are valproic acid, valpromide, valproate pivoxil, divalproex, sodium valproate and semi-sodium valproate, and more preferably sodium valproate. For the treatment of epilepsy, the recommended initial dose of valproate for an adult in Europe is 600 mg/day, increasing at 200 mg at three-day intervals until seizure control is achieved or adverse effects preclude further increases. The usual range is 1 to 2 g daily (20 to 30 mg per kg body weight per day), with a maximum daily dosage of 2.5 g. The daily dosage recommended for children weighing more than 20 kg is 20 to 30 mg/kg/day. In children weighing less than 20 kg, a dosage of 20 mg/kg/day is recommended; in case of required dosage above 40 mg/kg/day, clinical chemistry and haematological parameters should be monitored. For elderly, dosage requirements of valproate should be lower because of variations of pharmacokinetic parameters. For most patients, therapeutic plasma valproate concentrations will range from 40 to 100 μg/ml. The amount of the active ingredients (levetiracetam and compound inducing neural inhibition mediated by the $GABA_A$ receptors) in accordance with this aspect of the invention will vary depending on the mammal to which the compositions are administered, the disease to be treated, other active ingredients present, etc. Generally, the amount of the compound inducing neural inhibition mediated by the $GABA_A$ receptors and the amount of levetiracetam for a given composition and dosage form can be readily determined employing routine procedures.

Consequently, the present invention concerns a pharmaceutical composition comprising levetiracetam and at least one compound inducing neural inhibition mediated by the $GABA_A$ receptors.

The pharmaceutical composition of the present invention comprises an effective therapeutic amount of the compound inducing neural inhibition mediated by the $GABA_A$ receptors, and an effective therapeutic amount of levetiracetam preferably in a ratio between 2 and 15.

The pharmaceutical compositions according to the present invention can be administered orally or parenterally as described above.

Compositions comprising a reduced dose of valproate present also some interest.

The compositions of the present invention may be used for the treatment of epilepsy and for controlling seizures, for the treatment of depression, bipolar disorders, chronic or neuropathic pain and for the treatment of migraine and other diseases controlled with the compound inducing neural inhibition mediated by the $GABA_A$ receptors. The daily effective dosage required depends on the condition being treated and on the individual characteristics of the patient.

In the pharmaceutical compositions of the present invention, the amount of levetiracetam is at least sufficient to potentiate the activity of the compound inducing neural inhibition mediated by the $GABA_A$ receptors.

A preferred composition, comprises an amount of levetiracetam at least sufficient to reduce the amount of the compound inducing neural inhibition mediated by the GABAA receptors while maintaining the aimed therapeutic effect.

Another preferred composition comprises an amount of the compound inducing neural inhibition mediated by the $GABA_A$ receptors which if administered alone would not be therapeutically effective, and at least a sufficient amount of levetiracetam to obtain the desired therapeutic effect.

As mentioned in the example 4 below, the enhancement of the potency by the levetiracetam, means that the usual effective amount of the compound inducing neural inhibition mediated by the $GABA_A$ receptors may be reduced by a factor of about 3 to 15, while maintaining the desired therapeutic effect. As example, the usual range of valproate for epilepsy is 1 to 2.5 g daily, thus it is possible to reduce the daily amount of valproate between 70 mg and 180 mg and preferably between 70 mg and 140 mg when given with a sufficient amount of levetiracetam to obtain a therapeutic effect.

The sufficient amount of levetiracetam can be up to 2.5 times lower than the normal effective dose for mono-administration.

Therefore, the pharmaceutical composition of the present invention have a good activity but reduced adverse events compared to the use of the compound inducing neural inhibition mediated by the $GABA_A$ receptors, such as valproate alone, for controlling seizures.

The present invention concerns also a use of the pharmaceutical composition for the treatment of epilepsy, alcohol withdrawal, tremor, bipolar disorder, mania, obsessive compulsive disorder, panic disorder, anxiety and anxiety disorders, depression, migraine, headache, pain disorders, ischemia and head trauma.

The present invention concerns also a use of the pharmaceutical composition for the manufacture of a medicament for a therapeutic application in a disease chosen among epilepsy, alcohol withdrawal, tremor, bipolar disorder, mania, obsessive compulsive disorder, panic disorder, anxiety and anxiety disorders, depression, migraine, headache, pain disorders ischemia and head trauma.

The present invention concerns also a method for treatment of a human patient by using the pharmaceutical composition.

The present invention concerns also the pharmaceutical composition for use as a medicament for curing the said disease.

The present invention concerns also the use of the pharmaceutical composition for the manufacture of a medicament for a therapeutic application in the said disease.

The present invention concerns also the use of a pharmaceutical composition comprising levetiracetam for the treatment of a patient administered with an amount of at least one compound inducing neural inhibition mediated by the $GABA_A$ receptors, which if administered alone would not be therapeutically effective.

The present invention concerns also a method for manufacturing a medicament intended for therapeutic application in the said disease, characterized in that the pharmaceutical composition is used.

The present invention is also directed to methods of treating humans to alleviate disease by the administration of the pharmaceutical composition.

The present invention concerns also methods of treating humans to alleviate disease by the administration of an amount of levetiracetam at least sufficient to reduce the amount of the compound inducing neural inhibition mediated by the $GABA_A$ receptors needed to maintain the desired therapeutic effect.

The present invention concerns also a method for treating a patient administered with an amount of at least one compound inducing neural inhibition mediated by the $GABA_A$ receptors, which if administered alone would not be therapeutically effective, comprising administering to such a mammal a therapeutically effective amount of levetiracetam for the treatment of a disease chosen among epilepsy, alcohol withdrawal, tremor, bipolar disorder, mania, obsessive compulsive disorder, panic disorder, anxiety and anxiety disorders, depression, migraine, headache, pain disorders, ischemia and head trauma.

The present invention concerns also a method for treating a disease chosen among epilepsy, alcohol withdrawal, tremor, bipolar disorder, mania, obsessive compulsive disorder, panic disorder, anxiety and anxiety disorders, depression, migraine, headache, pain disorders, ischemia and head trauma, comprising administering to a mammal afflicted with such a condition a therapeutically effective amount of a composition as described above for treating such condition.

The present invention concerns also methods for treating a patient administered with a non effective amount of at least one compound inducing neural inhibition mediated by the $GABA_A$ receptors comprising administering to such a mammal a therapeutically effective amount of levetiracetam.

By non effective amount, is meant an amount of active ingredient, which if administered alone would not be therapeutically effective.

The present invention concerns also a method of selectively potentiating the therapeutic effect of a compound inducing neural inhibition mediated by the $GABA_A$ receptors without increasing undesired side effects associated therewith which comprises co-administration of an amount of valproate which if administered alone would not be therapeutically effective, with an amount of levetiracetam effective in producing the desired therapeutic effect.

By co-administration is meant, simultaneous, separate or sequential administration.

It is demonstrated that levetiracetam possesses the ability to effectively potentiate valproate, clonazepam, chlordiazepoxide and phenobarbital in pharmacological models. The potentiating effect of levetiracetam permits the amount of valproate or pharmaceutically acceptable salts thereof to be reduced, and therefore the adverse events related to a valproate therapy to be reduced. Thus, patients obtaining an improvement of their symptoms at the expense of marked adverse effects during monotherapy treatment with valproate may obtain a significant improvement in their treatment outcome by combined dosing with a minor dose of valproate and levetiracetam. The same is the case for treatment with clonazepam, chlordiazepoxide and phenobarbital.

The potentiating effect of levetiracetam for valproate was evaluated in two different animals models of epilepsy: the sound-sensitive mice, a model of generalized epilepsy, and amygdala-kindled rats, a model of partial complex seizures with secondarily generalization. The impairment of performance within the rotarod test was also measured. Levetiracetam appears to potentiate the seizure protection obtained with valproate, clonazepam, chlordiazepoxide and phenobarbital, but not the adverse effects associated with valproate, clonazepam, chlordiazepoxide and phenobarbital.

A model of mania used to evaluate drug activity consists in an animal model of hyperreactivity induced by a mixture of dexamphetamine and chlordiazepoxide in rodents. This model was used to evaluate the antimanic properties of levetiracetam and valproate, taken alone or in combination, and underlined a supra-additive interaction between the two drugs.

The use of a combination therapy may be associated with an altered response and/or a higher incidence of adverse events and greater toxicity due to a modification of plasma and brain levels of drugs, i.e. a modification of pharmacokinetic parameters. A pharmacokinetic study realized with valproate, diazepam and phenobarbital alone or in combination with levetiracetam have shown a constant brain/plasma ratio. This demonstrates that the synergistic effect observed in pharmacological models between valproate, clonazepam, chlordiazepoxide and phenobarbital together with levetiracetam is not due to pharmacokinetic factors.

The administration of the pharmaceutical composition of the invention results in an improved reduction in the frequency and severity of diseases. The incidence of unwanted side effects can be reduced by the pharmaceutical composition of the invention in comparison to using higher doses of a compound inducing neural inhibition mediated by the $GABA_A$ receptors treatment to achieve a similar therapeutic effect.

The efficacy of levetiracetam for the treatment of migraine, bipolar disorders and chronic or neuropathic pains is illustrated by the results of the following pharmacological tests (examples 1 to 3). The potentiating effect of levetiracetam for compounds inducing neural inhibition mediated by the $GABA_A$ receptors and specifically for antiepileptic drugs, is illustrated by the results of the examples 4 to 7.

These examples illustrate the invention without in any way limiting its scope.

EXAMPLE 1

Pharmacological Data for the Treatment of Bipolar Disorders

Y Maze Test

An increase in motor activity is a frequent symptom of manic disorders and as a consequence, it is often used as a model of mania in laboratory animals. A wide variety of compounds or combinations of compounds can cause hyperactivity; however, not all forms of hyperactivity can be reversed by lithium. Further, not all activity tests are suitable for observing reproducible hyperactivity.

Hyperactivity induced in rodents tested in a symmetrical v maze by a mixture of dexamphetamine and chlordiazepoxide (DEX-CDP) has been used by a number of researchers to study the effect of lithium (Cox C. et al., "*Lithium attenuates "manic" activity in rats*" Nature (1971), vol. 232 p 336–338—Vale A. L. and Ratcliffe F., "*Effect of lithium administration on rat brain 5-hydroxyindole levels in a possible animal model of mania*" Psychopharamacol. (1987), vol.91 p 352–355), or more recently the effect of the antiepiteptic "Valproate" (Cao B. J. and Peng N. A., "*Magnesium valproate attenuates hyperactivity induced by dexamphetamine-chlordiazepoxide mixture in rodents*" Eur. J. Pharmacol. (1993), vol. 237, p 177–181). Those two compounds have been used clinically to treat bipolar disorders, i.e., acute mania and its management (see Gelenberg A. J. and Hopkins H. S "*Report on efficacy of treatments for bipolar disorder*" Psychopharmacol. Bull. (1993), vol. 29, p 447–4561 and have significantly reduced hyperactivity induced by DEX-CDP in rodents tested in a "Y" maze. Thus this model is acknowledged as a possible animal model for the study of mania.

The efficacy of (S)-(−)-α-ethyl-2-oxo-1-pyrrolidineacetamide for the treatment of mania has thus been studied using the model described above, using rats in which hyperactivity has been induced using the DEX-CDP mixture. Lithium and valproate were also tested and used as reference compounds.

The animals used were male Sprague-Dawley rats (origin: OFA, IFFA CREDO, Belgium) weighing between 210 and 290 grams. They were placed in stainless steel cages in groups of 8. The day prior to the experiment, they were placed in macrolon cages (4 animals per cage: 38×27×15 centimeters (cm)) with the floor covered with sawdust. The cages were placed in an animal holding chamber provided with air conditioning, illuminated from 0600 hrs to 1800 hrs. Food and water were available "ad libitum".

The apparatus used was a Y maze (each arm being 40 cm long and 15 cm wide with 35 cm walls) constructed from grey Plexiglass, located in a faintly illuminated room (Less than 5 Lux at ground level) and used to measure the rats' activity. The activity was estimated by recording the number of entries into the arms of the maze over a five-minute period. A video camera was positioned at a height of one meter above the apparatus and connected to a monitor located in an adjacent room in which an experimenter counted the number of entries into the arms.

The injection of different compounds into the rats was performed under the following conditions. 12.5 mg/kg of chlordiazepoxide and 1.18 mg/kg of D-amphetamine sulfate were dissolved in a saline solution (0.9%) and administered simultaneously by subcutaneous injection 35 minutes before the test in a volume of 1 ml/kg. 17 and 54 mg/kg of levetiracetam were dissolved in a saline aqueous solution (0.9%) and injected intraperitoneally 30 minutes before the test (table 4). 50, 100 and 200 mg/kg of sodium valproate were dissolved in an aqueous saline solution (0.9%) and injected intraperitoneally 15 minutes before the test (table 2). 2 and 4 milliequivalents (meq) of $Li^-$/kg of lithium chloride were dissolved in a saline solution (0.9%) and injected intraperitoneally 215 minutes before the test (table 1). The test drugs were injected in a volume of 5 ml/kg.

The effects of the different drugs were studied separately. In each experiment, the animals were placed in different groups (n=11 or 13/group) in a random fashion. During the test, each rat was placed in the center of the apparatus and the number of visits into the arms was recorded as an activity index.

For the results to be properly statistically analyzed, they were expressed as median with the first and third quartile. General comparisons of the statistics were carried out using a Kruskal-Wallis test for the controls and the effect of the compound per se. This test was also used to compare the effect of the (DEX-CDP) mixture, and the effect of the compounds against the hyperactivity induced by the (DEX-CDP) mixture.

In the event of a significant difference, multiple post hoc comparisons under the Kruskal-Wallis test were estimated using the method proposed by Siegel and Castellan (*Non parametric statistics*. McGraw Hill, second edition (1989)). Comparisons between the control group and the groups for the DEX-CPD mixture were carried out using the Mann-Whitney test (Non parametric statistics. McGraw Hill, second edition (1989)).

The results of these pharmacological studies are summarized and presented in Tables 1 to 4.

Administration of the DEX-CDP mixture induced a comparable and significant hyperactivity in each experiment.

Lithium chloride (table I) significantly counteracted the hyperactivity induced by DEX-CDP in a dose dependent manner. It even reduced the activity to below that of the non-hyperactive control rat. Lithium chloride per se induced a slight no significant reduction in the activity of non-hyperactive control.

TABLE I

| Treatment | Number of arms visited | P vs mixture | P vs control |
|---|---|---|---|
| Control | 26.5 (25.5–28) | 0.0005** | — |
| Mixture | 45 (39–48.5) | — | 0.0005** |
| Mixture + Lithium chloride 2 mEq/kg | 31.5 (27–36) | NS | — |
| Mixture + Lithium chloride 4 mEq/kg | 14 (10.5–17.5) | <0.001* | <0.0001** |
| Lithium chloride 2 mEq/kg | 25 (21–26.5) | — | NS |
| Lithium chloride 4 mEq/kg | 20 (16–23) | — | NS |

Effect of lithium chloride on hyperactivity induced by a mixture of chlordiazepoxide and D-amphetamine in a Y-maze test. Results are expressed in terms of median with Q1 and Q3 in parentheses.
*Multiple comparison test under Kruskal Wallis;
**Mann-Whitney test;
NS = no significant effect.
P = probability of the significant difference
P vs mixture = probability of the significant difference between the group tested and the mixture.

Sodium valproate (table II) significantly counteracted hyperactivity at a dose of 200 mg/kg. As was the case with lithium, sodium valproate tended to cause hypoactivity in the treated rats. Finally, it was observed that sodium valproate per se induced a strong dose dependent hyperactivity in non-hyperactive control.

TABLE II

| Treatment | Number of arms visited | P vs mixture | P vs control |
|---|---|---|---|
| Control | 25 (24–28) | <0.0001** | — |
| Mixture | 43 (34–44) | — | <0.0001** |
| Mixture + Sodium valproate 50 mg/kg | 38 (36–41) | NS | — |
| Mixture + Sodium valproate 100 mg/kg | 39 (32–41) | NS | — |
| Mixture + Sodium valproate 200 mg/kg | 20 (14–26) | <0.001* | 0.06** |
| Sodium valproate 50 mg/kg | 28 (24–31) | — | NS |
| Sodium valproate 100 mg/kg | 34 (32–36) | — | <0.05* |
| Sodium valproate 200 mg/kg | 40 (28–43) | — | <0.01* |

Effect of sodium valproate on hyperactivity induced by a mixture of chlordiazepoxide and D-amphetamine in a Y-maze test. Results are expressed in terms of median with Q1 and Q3 in parentheses.
*Multiple comparison test under Kruskal Wallis;
**Mann-Whitney test;
NS = no significant effect.
P = probability of the significant difference
P vs mixture = probability of the significant difference between the group tested and the mixture.

Levetiracetam (table III) significantly counteracted the hyperactivity induced by DEX-CDP at a dose of 54 mg/kg. Levetiracetam per se induced only a slight hyperactivity at a dose of 17 mg/kg.

Finally, an analysis of the experimental data showed a surprising normalization to the activity level of the non-hyperactive control rats when hyperactive rats (DEX-CDP) are treated with the highest dose of levetiracetam.

TABLE III

| Treatment | Number of arms visited | P vs mixture | P vs control |
|---|---|---|---|
| Control | 25 (22–29) | <0.0001** | — |
| Mixture | 40 (36–48) | — | <0.0001** |
| Mixture + Levetiracetam 17 mg/kg | 36 (32–38) | NS | — |
| Mixture + Levetiracetam 54 mg/kg | 26 (12–33) | <0.001* | NS |
| Levetiracetam 17 mg/kg | 31 (29–33) | — | <0.05* |
| Levetiracetam 54 mg/kg | 28 (26–28) | — | NS |

Effect of levetiracetam on hyperactivity induced by a mixture of chlordiazepoxide and D-amphetamine in a Y-maze test. Results are expressed in terms of median with Q1 and Q3 in parentheses.
*Multiple comparison test under Kruskal Wallis;
**Mann-Whitney test;
NS = no significant effect.
P = probability of the significant difference.
P vs mixture = probability of the significant difference between the group tested and the mixture.

Taken together, these results suggest that levetiracetam has an unexpected potential for the treatment of bipolar disorders.

EXAMPLE 2

Pharmacological Data for Treatment of Chronic or Neuropathic Pain Disorders

In order to study the activity of levetiracetam with respect to chronic or neuropathic pain, the Applicant carried out a series of experiments based on the Randall test "A method for measurement of analgesic activity on inflamed tissue; Arch. Int. pharmacodyn., 1957, CXI, No4. P 409–419". By virtue of this protocol, it was possible to determine the ability of levetiracetam to correct hyperalgesia secondary to induction of a neuropathic problem of metabolic origin in a rodent.

This study was performed with rats in which diabetes had been artificially induced by injecting streptozotocin. The diabetic neuropathy thereby induced allowed the correction of the hyperalgesia caused by the use of levetiracetam to be measured.

The animals used for these experiments were male Sprague-Dawley rats (Charles River, France), weighing 250–280 grams (g), which had undergone induction of diabetes one week after receipt. Male Sprague-Dawley rats (200–220 g) received one interperitoneal injection of streptozocin (75 mg/kg, i.p.) (Zanosar˙, Upjohn, France) dissolved in distilled water. Hyperglycaemia was confirmed one week after induction by determining the quantity of blood glucose (caudal puncture) using a Dextrostix reactive strip (Ames) read using a calorimeter (Ames Division, Miles Laboratoires, France). Animals with more than 14 millimoles (mM) were considered to be diabetic. The pain thresholds were determined 3 weeks after induction of diabetes. Only animals with a 15% reduction in the thresholds were selected.

This model was used in accordance with the description in COURTEIX et al., "*Streptozocin-induced diabetic rats. Behavioural evidence for a model of chronic pain*" Pain (1993), vol. 53, p81–88. The study was performed using the following compounds:

LEVETRACETAM: (Laboratories UCB), dissolved in distilled water.

CARBAMAZEPINE: (Sigma), dissolved in hydroxy propel methylcellulose.

As has already been mentioned above, the test explained below was performed to stimulate a reaction in the animal with a mechanical nociceptive stimulus to a hind paw. An increasing pressure was applied using an analgesia meter (Ugo Basile, type 7200), until a cry was emitted which was considered to be the pain threshold, expressed in grams.

The experimental protocol and parameters measured are defined as follows.

After determining the base thresholds, the animals received the study treatments (vehicle, levetiracetam, 17, 54, 95.2 and 120 mg/kg, carbamazepine, 10 and 30 mg/kg) administered intraperitoneally (i.p.) using the equal block method to avoid any chronobiological influence. The effects of different treatments were thus determined during the same time period. The reaction thresholds were measured 15, 30, 45, 60, 90, 120 and 180 minutes (min) after administration. All of the experiments were performed blind with 8 different animals per treatment.

TABLE A

Performed treatments

| Group | Test | No. of treated rats | Compound | Dose (mg/kg) | Administration Route | Volume |
|---|---|---|---|---|---|---|
| 1 | Randall and Selitto | 56 | Levetiracetam | 17; 54; 95.2; 120 | i.p. | 2 ml/kg |
|  |  | 56 | Carbamazepine Vehicle | 10; 30 |  |  |

No = number
i.p. = intraperitoneal

The results are expressed as means±standard error of mean (S.E.M.).

The dose which could overcome 50% of the hyperalgesia induced by diabetes was calculated as the "anti-hyperalgesic dose effective 50".

Statistical comparison was carried out by means of a two-way analysis of variance followed by Fischer's PLSD multiple comparison test to analyze the temporal effect.

By normal animal, the applicant means, animal in which no diabetes has been induced.

A study of the data obtained bay the Applicant has revealed the following facts.

Induction of diabetes was accompanied by mechanical hyperalgesia, confirmed in all of the animals used by a significant reduction in the vocalization thresholds from 309.4±15.2 g to 152.8±8.0 g. Injecting the vehicle did not significantly modify the vocalization thresholds (Table B).

In this test (Table B), a dose of 120 mg/kg of levetiracetam caused complete correction of hyperalgesia manifested by a statistically significant increase in the vocalization thresholds, at a maximum 15 min after injection, and persisting up to 60 min after injection. The increase in the thresholds observed with the 3 other doses was also significant from 15 minutes after injection up to 45 min for doses of 95.2 and 54 mg/kg and 30 min for the dose of 17 mg/kg. The anti-hyperalgesic effective dose 50 was 35.1±1.8 mg/kg.

Carbamazepine used as the positive control caused a complete reversal of diabetic hyperalgesia for the 2 doses used (Table B). It became anti-hyperalgesic from fifteen minutes after injection of the dose of 30 mg/kg, an effect that persisted to the ninetieth minute.

The dose of 10 mg/kg only caused a reversal in hyperalgesia in the thirtieth minute after injection, the effect being maintained for sixty minutes.

These data also confirm that the active dose 30 mg/kg of carbamazepine altered the threshold of animals to a level far above the level of normal animals (i.e. response before induction of diabetes), which could be detrimental to an adaptive pain feeling.

It should be noted that at a dose of 30 mg/kg, carbamazepine induced, with a delayed effect (30 min after injection), a reduction in spontaneous motor activity (which we did not quantify). Nevertheless, this could imply that at this dosage, carbamazepine has side effects like sedation, akinesia, or ataxia.

Taken together, these results suggest that levetiracetam has an unexpected potential as a drug for the treatment and or prophylactic treatment of chronic or neuropathic pains.

TABLE B

EFFECT OF LEVETIRACETAM AND CARBAMAZEPINE ON HYPERALGESIA IN DIABETIC RATS

| COMPOUNDS | BEFORE DIABETES | AFTER DIABETES | | | | | | | |
|---|---|---|---|---|---|---|---|---|---|
|  |  | 0[+] | 15 | 30 | 45 | 60 | 90 | 120 | 180 |
| Vehicle | 306.6 (10.93) | 174.4 (4.19) | 180.0 (2.83) | 183.8 (4.70) | 181.9 (5.97) | 166.9 (3.40) | 166.9 (5.97) | 166.9 (5.26) | 166.9 (4.43) |
| Levetiracetam 17 mg/kg | 282.2 (5.48) | 181.9 (3.09) | 211.9 (7.19)* | 206.3 (10.12)* | 193.1 (7.19) | 185.6 (4.86) | 178.1 (3.40) | 180.0 (2.83) | 176.3 (2.45) |
| Levetiracetam 54 mg/kg | 296.3 (10.12) | 180.0 (5.30) | 238.1 (22.04)* | 243.8 (15.97)* | 230.6 (14.44)* | 189.4 (13.87) | 176.3 (8.39) | 176.3 (6.80) | 176.3 (6.80) |
| Levetiracetam 95.2 mg/kg | 306.6 (11.73) | 169.7 (6.00) | 264.4 (13.58)* | 283.1 (24.62)* | 234.4 (11.32)* | 180.0 (12.36) | 180.0 (8.02) | 159.4 (3.95) | 163.1 (4.43) |
| Levetiracetam 120 mg/kg | 309.4 (15.25) | 161.3 (7.23) | 331.9 (31.75)* | 315.0 (30.00)* | 262.5 (27.04)* | 213.8 (13.52)* | 176.3 (7.36) | 174.4 (6.30) | 168.8 (4.70) |
| Carbamazepine 10 mg/kg | 300.9 (12.31) | 170.6 (5.26) | 217.5 (18.59)* | 333.8 (14.66)* | 273.8 (12.60)* | 206.3 (10.51)* | 187.5 (8.02) | 174.4 (3.95) | 174.4 (3.95) |
| Carbamazepine 30 mg/kg | 280.3 (9.92) | 152.8 (8.01) | 450.0 (44.10)* | 425.6 (39.98)* | 311.3 (36.05)* | 230.6 (24.86)* | 196.9 (14.01)* | 174.4 (7.99) | 170.6 (6.30) |

Effect of Levetiracetam and Carbamazepine on vocalization threshold (g) in diabetic rats.
Results are expressed in terms of mean with SEM between brackets.
* = significant difference from controls (vehicle).
[+] = time after injection of Levetiracetam and Carbamazepine (minutes.).

EXAMPLE 3

Pharmacological Data for the Treatment of Migraine

To show the efficacy and safety of oral tablets of levetiracetam for the treatment of migraine, a clinical study such as described below is launched.

The primary objective of this therapeutic exploratory study is to evaluate the efficacy and safety of 750 mg b.i.d. levetiracetam for the prevention of migraine headache, with or without aura, as defined by the IHS (Headache Classification Committee of the International Headache Society (IHS) "Classification and diagnostic criteria for headache disorders, cranial neuralgias, and facial pain"; Cephalalgia (1988), No 8 (Suppl. 7), p 19–28.

This 18-week study employs a multicenter, randomised, placebo controlled, parallel group design. The study consists of a 4-week single-blind placebo Baseline Period, a 12-week double-blind Evaluation Period, and a Post-Treatment Period where a final study visit occurs two weeks after the last dose of study drug. Study visits are performed 4-weekly with a window of +/- one week. This study randomises subjects who experience 3–8 migraine headaches per 4 weeks during the Baseline Period, with or without aura, as defined by the IHS. Each randomised subject must have experienced migraine headache symptoms for more than 1 year prior to randomisation and must have at least a 3 month documented medical history of migraine headaches in the subject chart. This study enrols 80 subjects at approximately 8 centres.

Levetiracetam is studied over a longer study period (approximately 4 months), to assess the prophylactic (preventive) effect and/or the abortive (suppressive) effects of the medication. Patients enrolled in this study are chronic migraine sufferers who meet the diagnostic criteria as proposed by the IHS. The primary efficacy parameter to assess the prophylactic effect of the treatment is assessed by measuring the decrease in frequency of migraine events, comparing the 3-month Evaluation Period (treatment with either levetiracetam or placebo) with the 4-week baseline (patients experiencing between 3 and 8 attacks/month). Additional efficacy endpoints include responder rate (number of patients in each group with a reduction of 50% or more in migraine attacks), number of migraine free-days, and the impact of migraine attacks on the patient's daily functioning and qualify of life (MIDAS scale and Migraine Specific Quality of Life Questionnaire).

EXAMPLE 4

Interaction Between Levetiracetam and Valproate in Preventing AUDIOGENIC-Induced Clonic Convulsions in and Evaluation of the Adverse Effects with the Rotarod Test The purpose of this study was to evaluate the effect of levetiracetam on the anticonvulsivant potency of valproate in sound sensitive mice, a genetic animal model with reflex seizures. In this model of generalized epilepsy, seizures can be evoked without electrical or chemical stimulation and seizure types, at least in part, are similar in their clinical phenomenology to seizures occurring in man (Löscher W. & Schmidt D., Epilepsy Res. (1988), 2, 145–181; Buchhalter J. R., Epilepsia (1993), 34, S31–S41).

Male genetically sound-sensitive mice (15–29 g; N=10), derived from a DBA strain originally selected by Dr Lehmann of the Laboratory of Acoustic Physiology (Paris) and bred in the UCB Pharma Sector husbandry unit since 1978, were submitted on one hand to the induction of audiogenic seizures, and on the other hand to a rotating rod test. The experimental design consisted of one group receiving vehicles, another group receiving levetiracetam alone at a dose of 5.5 mg/kg and the other groups receiving different doses of valproate alone or in combination with levetiracetam. Levetiracetam alone was also tested. Levetiracetam and valproate, in a dose-volume of 10 ml/kg body weight, were administered intraperitoneally 60 and 30 minutes, respectively, before the induction of audiogenic seizures or the measurement of rotarod performance. Levetiracetam and sodium valproate were both dissolved in 0.9% saline solution, to give solutions of pH 6.4 and 6.2, respectively.

For audiogenic seizure testing, the mice were placed in the cages, one mouse per cage, in the sound-attenuated chamber. After a period of habituation of 30 seconds, the acoustic stimulus (90 dB, 10–20 kHz) was delivered for 30 seconds via the loud speakers. During this interval, the mice were observed and the presence of the 3 phases of the seizure activity, namely wild running, clonic and tonic convulsions, was recorded. The proportion of mice protected against clonic convulsions was calculated and used as the end point for the anticonvulsant activity.

For rotarod testing, the mice were placed on the rotating rod and the animals that were unable to remain on the rod for at least 60 seconds were considered as having an impaired performance.

Methods used for calculation and statistical analysis are described hereafter:

A response to drug treatment was expressed as the proportion of animals protected against induced convulsions, or showing an impairment of the rotarod performance, at each individual dose. When similar doses of the same compound were tested in independent experiments, their results were (Chi-Square test for homogeneity of proportions) and combined in case of non significance ($P>0.05$).

Dose-response curves of individual compounds were fitted in the form of a LOGIT-LOG DOSE linear weighted regression. A Chi-Square test of goodness of fit was used to assess adequacy of the fitting procedure.

When the dose of levetiracetam associated with valproate was considered as inactive by itself, an ordinary LOGIT-LOG DOSE regression as above was fitted. If the dose of levetiracetam has been proved to be active by itself, the observed proportions for mixtures were corrected by subtracting the effect due to levetiracetam by following principally the Abbott's method (Roberts M. & Boyce C.B.C., Methods in Microbiology (1972), Eds. Norris J. R. & Ribbons D. W. Academic Press. Vol 7A, 153–189) and the Bartholomew's method (Fleiss J. L., Statistical methods for rates and proportions. 2nd edition (1981). Eds. Wiley J. and Sons).

Two theoretical models of interaction were used to evaluate the combined effects of valproate and levetiracetam: the additive model and the independent model. Effects will be defined as additive when replacement of part of the dose of on drug by another, in an amount proportionate to the relative potency of the drugs, maintains the same effect (Plummer J. L. & Short T. G., J. Pharmacol. Methods (1990), 23, 297–309). The independent model is based on different modes of action for the two drugs (Chou T. C. & Talalay P., Adv. Enz. Regul. (1984), 22, 27–55). In these models, a difficulty arises when the slopes (the HILL-like coefficients) of the dose-response curves are different. However, by applying the median-effect principle, which forms the theoretical basis of the models, it may be shown that in the restricted condition, where p=0.5 (50% protection). the value of the slopes can be ignored. The derived formulation of the theoretical models are:

$$\frac{Vm_{50}}{V_{50}} + \frac{Lm_{50}}{L_{50}} = 1$$

for the additive model, $$\frac{Vm_{50}}{V_{50}} + \frac{Lm_{50}}{L_{50}} + \frac{Vm_{50} \times Lm_{50}}{V_{50} \times L_{50}} = 1$$

for the independent model, where $Vm_{50}$ and $Lm_{50}$ are the doses of valproate and levetiracetam, respectively, in a mixture that should result in a 50% protection; $V_{50}$ and $L_{50}$ are the EDso values of valproate and levetiracetam, respectively, when tested alone. From these formulations, the dose of valproate, considered as expected value, that should be associated to a constant dose of levetiracetam in order to afford 50% of protection, may be calculated as:

$$Vm_{50} = V_{50} \times \left(1 - \frac{Lm_{50}}{L_{50}}\right)$$

for the additive model $$Vm_{50} = V_{50} \times \left(\frac{L_{50} - Lm_{50}}{L_{50} + Lm_{50}}\right)$$

for the independent model.

These calculated doses ($Vm_{50}$ expected) may then be compared to the observed doses of valproate which, in combination with a constant dose of levetiracetam, induce an effect corresponding to 50% protection ($Vm_{50}$ observed). In case of a supra-additive effect, the ratio $Vm_{50}$ expected/$Vm_{50}$ observed is greater than 1 and may be considered as a measure of the reduction of the dose of valproate, in presence of levetiracetam, needed to afford 50% protection.

An alternative approach, the "non-parallel dose-response curves method" (Plummer J. L. & Short T. G., J. Pharmacol. Methods (1990), 23, 297–309), which does not restrict the comparison of observed and predicted responses to the particular condition defined by p=0.5 and takes into account the different slopes of the individual dose-response curves of the two compounds to be combined, was also employed. Accordingly, expected responses were calculated for each tested mixture of valproate and levetiracetam and compared to observed responses, a comparison from which a diagnosis of the type of interaction (additivity—supra-additivity—antagonism) may be proposed for various levels of effects and doses. Where the number of dose combinations tested was high enough, a rough statistical test was used to assess significance of the results based upon the proportion of mixtures showing consistent directional divergences between observed and expected responses (Two-sided Binominal Test considering random positive and negative, differences between observed and expected results as null hypothesis).

Audiogenic seizure testing results are as follows:
The estimated parameters from the linearized LOGIT-LOG DOSE regression are presented in table xx1.

TABLE xx1

|  | Valproate | Levetiracetam |
|---|---|---|
| $ED_{50}$ (mg/kg) | 122 | 10 |
| Slope | 4.29 | 2.29 |

From the dose-response relation adjusted to the results of levetiracetam alone, it was inferred that the dose of 5.5 mg/kg of levetiracetam has a significant activity by itself: 20% of animals are protected by this dose. This proportion was taken into account for correcting the observed proportions of protected animals with mixtures, as explained above. The dose of valproate, in combination with 5.5 mg/kg of levetiracetam, able to afford protection against audiogenic-induced clonic convulsions in 50% of the animals was estimated from the resultant adjusted curve: $Vm_{50}$ observed=3.9 mg/kg Results obtained from the additive and the independent theoretical models of interaction are presented in table xx2 and may be interpreted as supra-additive interaction. A nine to fourteen reduction of the valproate dose needed to protect 50% of the animals against audiogenic-induced clonic convulsions was obtained in the presence of levetiracetam. This result may be interpreted as a supra-additive interaction.

TABLE xx2

|  | $Vm_{50}$ expected | $Vm_{50}$ observed | $\frac{Vm_{50} \text{ expected}}{Vm_{50} \text{ observed}}$ |
|---|---|---|---|
| Additive model | 54.9 | 3.9 | 14.1 |
| Independent model | 35.4 | 3.9 | 9.1 |

Impairment of performance within the rotarod test is as follows:
The estimated parameters from the linearized LOGIT-LOG DOSE regression are presented in table xx3.

TABLE xx3

|  | Valproate | Levetiracetam |
|---|---|---|
| $ED_{50}$ (mg/kg) | 178.5 | 360.7 |
| Slope | 2.21 | 0.77 |

From the dose-response relation adjusted to the results of levetiracetam alone, it was inferred that the dose of 5.5 mg/kg of levetiracetam has a slight activity by itself: 4% of animals showed an impairment of the rotarod performance. This proportion was taken into account for the fitting of a curve relating the response to valproate doses associated to levetiracetam in the form of a LOGIT-LOG DOSE. From this adjusted curve, dose of valproate, in combination with 5.5 mg/kg of levetiracetam, able to produce an impairment of the rotarod performance in 50% of the animals was estimated $Vm_{50}$ observed=127.5 mg/kg The values $Vm_{50}$ expected were calculated according to the additive and the independent theoretical models, and were compared to the corresponding observed doses of valproate (table xx4). A slight reduction of the valproate dose needed to produce an impairment of the rotarod performance in 50% of the animals was obtained in the presence of levetiracetam, a result that may suggest a modest supra-additive interaction.

TABLE xx4

|  | $Vm_{50}$ expected | $Vm_{50}$ observed | $\dfrac{Vm_{50} \text{ expected}}{Vm_{50} \text{ observed}}$ |
|---|---|---|---|
| Additive model | 175.8 | 127.5 | 1.38 |
| Independent model | 173.1 | 127.5 | 1.36 |

Conclusions are as follows:

This study reveals an unexpected, supra-additive interaction in the protection afforded by combined dosing with valproate and levetiracetam against audiogenic-induced clonic convulsions in sound-sensitive mice. A minor supra-additive interaction cannot be excluded in the impairment of performance within the rotarod test but this interaction clearly appears more discrete as shown by the ratio $Vm_{50}$ expected/$Vm_{50}$ observed in the following table (table xx5).

TABLE xx5

|  |  | Audiogenic seizure testing | Rotarod test |
|---|---|---|---|
| $\dfrac{Vm_{50} \text{ expected}}{Vm_{50} \text{ observed}}$ | additive model | 14.1 | 1.4 |
| $\dfrac{Vm_{50} \text{ expected}}{Vm_{50} \text{ observed}}$ | independent model | 9.1 | 1.4 |

The therapeutic ratio of valproate within sound-sensitive mice is low due to a minimal separation in the doses protecting against sound-induced clonic convulsions ($ED_{50}$=122 mg/kg) and impairing the rotarod-performance ($TD_{50}$=178 mg/kg). However, the supra-additive interaction in the protective effect against clonic convulsions and the minor interaction observed within the rotarod test enables consistent seizure protection after combined dosing with valproate and levetiracetam with the advantage that the dose of valproate, and thereby the impairment obtained within the rotarod test, can be reduced markedly (table xx6).

TABLE xx6

| Treatment inducing protection within 50% of the sound-sensitive mice against the audiogenic same-induced clonic convulsions. | Impairment in the performance within the rotarod test obtained after treatment. |
|---|---|
| Valproate (122 mg/kg) + saline | 30% |
| Valproate (3.9 mg/kg) + levetiracetam) <(5.5 mg/kg | 0.1% |

Similar experiments were performed in order to evaluate the interaction between levetiracetam and other GABAergic agents, namely clonazepam, chlordiazepoxide and phenobarbital.

Levetiracetam potentiated the anticonvulsant activity afforded by clonazepam, chlordiazepoxide and phenobarbital in sound-sensitive mice. The dose needed to protect 50% of the animals against audiogenic-induced clonic convulsions was significantly reduced when combining 5.5 mg/kg of levetiracetam with clonazepam (reduced by a factor of 4.5 to 7.0), chlordiazepoxide (reduced by a factor of 3.7 to 5.8) and phenobarbital (reduced by a factor of 3.5 to 5.5). This supra-additive interaction was not associated with a similar increase in adverse effects potential. As for valproate, the impairment of rotarod performance induced by clonazepam, chlordiazepoxide and phenobarbital was not affected by combined treatment with a dose of 5.5 mg/kg levetiracetam.

EXAMPLE 5

Interaction Between Levetiracetam and Valproate in Secondary Generalized Motor Seizure in Amygdala-Kindled Rats and Evaluation of the Adverse Effects with the Rotarod Test The purpose of this study was to evaluate the pharmacodynamic interaction between valproate levetiracetam in preventing secondarily generalized motor seizures in amygdala-kindled rats, a model that has repeatedly been proposed to reflect complex partial seizures with secondarily generalization in man (Löscher W. & al., Exp. Neurol. (1986), 93, 211–226; McNamara J. O., Ann. of Neurol. (1984), 16 (suppl.), S72–S76).

In this model, focal electrical kindling of amygdala in rats induces the development of electrical seizure activity (afterdischarges) in amygdala and behavioral seizures, generally evolving through facial clonus, head nodding, forelimb clonus, rearing and fully kindled seizures with rearing and falling accompanied by generalized clonic seizures (Racine R. J., Electroencephalogr. Clin. Neurophysiol. (1972), 32, 281–294).

Kindling was induced in male Sprague Dawley rats (200–250 g) by following the method described by Löscher (Löscher W. & al., Exp. Neurol. (1986), 93, 211–226).

Levetiracetam and valproate, in a dose-volume of 5 ml/kg body weight, were administered intraperitoneally 60 and 30 minutes, respectively, before the induction of kindling or the measurement of rotarod performance. Levetiracetam (17, 54 and 10.8 mg/kg) and sodium valproate (50, 100, 150, 200 and 300 mg/kg) were both dissolved in 0.9% NaCl to give solutions of pH 5.9 and 6.3, respectively. Control rats received an equivalent dose-volume of the appropriate vehicle.

For the kindling experiments, all kindled animals (n=8) were stimulated once with the same stimulation parameters as used for the induction of kindling, 60 and 30 minutes after intraperitoneal administration of saline. Two days later, drugs were tested. The behavioral effect of stimulation was graded according to the score of Racine (Racine R. J., Electroencephalogr. Clin. Neurophysiol. (1972), 32, 281–294). The proportion of rats protected against secondarily generalized motor seizures (a score of either 3, 4 or 5) was calculated for each group and used as end point for anticonvulsant activity.

The amygdala-kindled rats (n=8) were also tested on a rotating rod. The animals were pretreated with i.p. administrations of levetiracetam and valproate 60 and 30 minutes, respectively, before testing, Only animals that were unable to remain on the rod after three subsequent 1-minute attempts were considered as having an impaired performance. Results were analyzed as described in example 1.

Protection against secondarily generalized motor seizures is as follows:

The estimated parameters from the linearized LOGIT-LOG DOSE regression are presented in table xx7:

TABLE xx7

|  | Valproate | Levetiracetam |
|---|---|---|
| $ED_{50}$ (mg/kg) | 197 | 307 |
| Slope | 5.38 | 0.88 |

From the dose-response relation adjusted to the results of levetiracetam alone it was inferred that each of these doses has a significant activity by itself. Calculated proportions of animals protected by these three doses of levetiracetam alone are 7, 18 and 28.5%, respectively. These proportions were taken into account for correcting the observed proportions of protected animals with mixtures, as explained precedently. From the adjusted curves, the doses of valproate able to afford protections against secondarily generalized motor seizures in 50% of the animals in the presence of 17, 54 or 108 mg/kg of levetiracetam, respectively, were estimated (table xx8).

TABLE xx8

|  | $Vm_{50}$ observed (mg/kg) |
|---|---|
| Valproate + 17 mg/kg of levetiracetam | 68.5 |
| Valproate + 54 mg/kg of levetiracetam | 27.5 |
| Valproate + 108 mg/kg of levetiracetam | 26.5 |

Doses of valproate that affords protection against secondarily generalized motor seizures in 50% of the animals when associated with constant doses of levetiracetam were calculated according to the additive and the independent theoretical models. Results of these calculations ($Vm_{50}$ expected) are presented in table xx9, where they are compared to the corresponding doses of valproate, observed to give 50% protection when associated with levetiracetam ($Vm_{50}$ observed). A three to five fold reduction of the valproate dose needed to protect 50% of the animals may be obtained in the presence of levetiracetam, a result that may be interpreted as a supra-additive interaction.

TABLE xx9

|  | Additive model | | Independent model | |
|---|---|---|---|---|
|  | $Vm_{50}$ expected | $\dfrac{Vm_{50} \text{ expected}}{Vm_{50} \text{ observed}}$ | $Vm_{50}$ expected | $\dfrac{Vm_{50} \text{ expected}}{Vm_{50} \text{ observed}}$ |
| Valproate + levetiracetam 17 mg/kg | 186 | 2.7 | 176.4 | 2.6 |
| Valproate + levetiracetam 54 mg/kg | 162 | 5.9 | 138 | 5.0 |
| Valproate + levetiracetam 108 mg/kg | 127.8 | 4.8 | 94.6 | 3.5 |

Impairment of performance within the rotarod test is as follows:

Valproate estimated parameters from the linear LOGIT-LOG DOSE regression are presented in table xx10. None of the three doses of levetiracetam tested (108, 170 and 540 mg/kg) impaired the performance of the amygdala-kindled rats in this test and the doses of levetiracetam used in combination with valproate (108 and 170 mg/kg) were therefore considered as inactive.

TABLE xx10

|  | Valproate |
|---|---|
| $ED_{50}$ (mg/kg) | 205 |
| Slope | 3.64 |

Independent LOGIT-LOG VALPROATE DOSE regressions were fitted to the results obtained in the presence of these two constant doses of levetiracetam: 108 and 170 mg/kg. Parameters estimated from these fittings are reported in table xx11.

TABLE xx11

|  | $Vm_{50}$ observed (mg/kg) |
|---|---|
| Valproate + 108 mg/kg of levetiracetam | 161 |
| Valproate + 170 mg/kg of levetiracetam | 174 |

A slight leftward shift was observed in the dose-response curves when valproate was associated with levetiracetam. However, no consistent dose-related effects of levetiracetam was present, as could be anticipated with a drug inducing a supra-additive effect. A comparison of the $Vm_{50}$ values for valproate, estimated from these dose-response curves, substantiates this observation (205, 161 and 174 mg/kg for the 0, 108 and 170 mg/kg doses of levetiracetam combined with valproate).

Conclusions are as follows:

This study reveals an unexpected, supra-additive interaction in the protection afforded by combined dosing with valproate and levetiracetam against the expression of secondarily generalized motor seizures in amygdala kindled rats. In contrast, no significant interaction was observed with regard to adverse effects quantified by performance within the rotarod test. The latter was to be expected since the doses of levetiracetam used were inactive themselves within this test.

The therapeutic ratio of valproate within amygdala-kindled rats is limited with nearly identical doses resulting in protection against secondarily generalized motor seizures ($ED_{50}$=197 mg/kg) and impairment in the rotarod test ($TD_{50}$=205 mg/kg). However, the supra-additive interaction against the secondarily generalized motor seizures and the lack of any significant interaction within the rotarod test enables consistent seizure control after combined dosing with valproate and levetiracetam with the advantage that the dose of valproate, and thereby the impairment obtained within the rotarod test, can be reduced markedly (table xx12).

TABLE xx12

| Treatment inducing protection within 50% of the amygdala-kindled rats against the expression of secondarily generalized motor seizures | Impairment in the performance within the rotarod test obtained after the same treatment |
|---|---|
| Valproate (197 mg/kg) + saline | 46% |
| Valproate (68.5 mg/kg) + levetiracetam (17 mg/kg) | 2% |
| Valproate (27.5 mg/kg) + levetiracetam (54 mg/kg) | <0.1% |
| Valproate (27 mg/kg) + levetiracetam (108 mg/kg) | <0.1% |

On an other hand, the activity curve comparison of levetiracetam alone or in combination with valproate leads to the conclusion that the use of a combination of the two drugs is always interesting, even if levetiracetam high doses are employed. The dose effect curve slope of levetiracetam is very small, that means that 100% of animals could be protected against induced-convulsions, but with very high doses of levetiracetam. The addition of a small amount of valproateallows 100% of animals to be protected with more acceptable doses of levetiracetam.

EXAMPLE 6

Attenuation of Hyperreactivity Induced by a Mixture of Dexamphetamine-Chlordiazepoxide in the Rat The purpose of the present experiment was to study the effects of levetiracetam administered alone or in combination with valproate on the hyperactivity induced in rats by a mixture of dexamphetamine-chlordiazepoxide (DEX-CDP) evaluated in a Y-shaped maze apparatus, a test recognized as a model for mania. Increased motor activity is a frequent symptom of manic disorders and, therefore, is often used as a model of mania in laboratory animals. Lithium, a medicine approved by the FDA in the prophylaxis and the treatment of bipolar disorders and mania, and valproate, indicated for the treatment of manic episodes associated with bipolar disorders, have been shown active in this model of mania (Vale A. L. & Ratcliffe F., Psychopharmacol. (1987), 91, 352–355; Cao B. J. & Peng N. A., Eur. J. Pharmacol. (1993), 237, 177–181).

Hyperactivity was induced in male Sprague Dawley rats weighing 210–290 g (n 13 or 15 per group) by a mixture of dexamphetamine-chlordiazepoxide as described by Vale A. L. (Vale A. L. & Ratcliffe F., Psychopharmacol. (1987), 91, 352–355). Chlordiazepoxide 12.5 mg/kg and D-amphetamine sulfate 1.18 mg/kg were dissolved in saline solution (0.9%) and coadministered subcutaneously 35 minutes before testing in a volume of 1 ml/kg. Levetiracetam 17 mg/kg was dissolved in saline solution (0.9%) and injected i.p. 30 minutes before testing. Sodium valproate 150 mg/kg was dissolved in saline solution (0.9%) and injected i.p. 15 minutes before testing. The test drugs were injected in a volume of 5 ml/kg.

Each rat was placed in the center of the Y-maze (with each arm 40 cm long and 15 cm wide with 35 cm walls) constructed in gray plexiglas. The number of visits into the arms was recorded over a 5 minutes period as an index of activity.

The results were expressed as median with the first and third quartile. Overall statistical comparisons were made using the Kruskal Wallis test for the effect of the compounds per se on the one hand, and for the effect of the compounds against the mixture induced-hyperactivity on the other hand. In a case of a significant result, post hoc multiple comparisons under the Kruskal Wallis test were computed following the method proposed by Siegel and Castellan (Siegel S. & Castellan N. J., Non parametric statistics (1989), Mac Graw Hill, Second Edition). Comparison between control group and DEX-CDP mixture group was made using the Mann-Whithney test.

A possible interaction between levetiracetam and valproate against DEX-CDP induced hyperactivity was evaluated by combining inactive doses of levetiracetam (17 mg/kg) and sodium valproate (150 mg/kg) (table xax1). The combination between levetiracetam 17 mg/kg and valproate 150 mg/kg induced an important effect against the hyperactivity induced by the DEX-CDP mixture. The effect of the combination was statistically significant (p<0.05) while effects of levetiracetam 17 mg/kg and valproate 150 mg/kg given alone were not different from effects observed in the group of animals administered with the mixture alone. The animals treated with the combination of levetiracetam and valproate were not different from the control animals not treated with the mixture.

TABLE xax1

Effect of levetiracetam and valproate on hyperactivity-induced by a mixture of chlordiazepoxide plus D-amphetamine in a Y-maze test.

| Treatment | n | Number of arms visited | p vs mixture | p vs mixture + Levetiracetam 17 + valproate 150 |
|---|---|---|---|---|
| Control | 13 | 23 (20–28) | <0.001** | NS** |
| Mixture[1] | 13 | 48 (44–51) | — | <0.05* |
| Levetiracetam 17mg/kg + Valproate 150 mg/kg + mixture[1] | 13 | 16 (14–25) | <0.05* | — |
| Levetiracetam 17 mg/kg + mixture[1] | 13 | 46 (41–49) | NS | <0.05* |
| Valproate 150 mg/kg + mixture[1] | 13 | 41 (18–49) | NS | <0.05* |

Results are expressed in terms of median with Q1 and Q3 in parentheses.
*Multiple comparisons tests under Kruskal Wallis ;
**Mann-Whitney test.
NS = not significant effect,
P = probability of the significant difference,
P vs mixture: probability versus DEX-CDP mixture (probability of the significant difference between the group tested and the mixture).
[1]: Mixture = DEX-CDE mixture.

EXAMPLE 7

Plasma and Brain Levels—Interaction Between Levetiracetam and Valproate in Preventing Audiogenic Seizure in Mice The aim of this pharmacological study was to investigate possible interactions between levetiracetam and valproate.

Male genetically sound-sensitive mice (17–30 g; N=10), derived from a DBA strain originally selected by Dr Lehmann of the Laboratory of Acoustic Physiology (Paris) and bred in the UCB Pharma Sector husbandry unit since 1978, were submitted to the induction of audiogenic seizures.

Levetiracetam (5.4 mg/kg) and sodium valproate (166.2 mg/kg) were administered orally, alone or in combination, 60 minutes before the induction of audiogenic seizures. For testing audiogenic seizure, the mice were placed in the cages, one mouse per cage, in the sound-attenuated chamber. After a period of habituation of 30 seconds, the acoustic stimulus (90 dB, 10–20 kHz) was delivered for 30 seconds via the loud speakers. During this interval, the mice were observed and the presence of the 3 phases of the seizure activity, namely wild running, clonic and tonic convulsions, was recorded.

In all animals, blood samples were collected immediately after the seizure test (I h after dosing) by cardiac puncture under light carbon dioxide anesthesia, into heparinised microtubes. The samples were centrifuged at 12000 r.p.m. for 5 minutes and the separated plasma was transferred into polypropylene microtubes and stored frozen at −20° C. Whole brains were removed at the same time, frozen in liquid nitrogen and stored at −20° C. Half of these samples were used for the determination of levetiracetam concentrations, the other half for the determination of valproate concentrations. Levetiracetam was measured in plasma and brain samples by validated gas chromatography assay with mass detection. With sodium valproate, fluorescence polarization immunoassays were used.

TABLE xx13

|  | Method-detection | Limits of quantitation | |
|---|---|---|---|
|  |  | plasma ($\mu$g/ml) | brain ($\mu$g/mg) |
| Levetiracetam | GC-MS | 0.02 | 0.4 |
| Valproate | FPIA | 43.2 | 43.2 |

The mean value plus standard deviation was calculated for plasma and brain concentrations of valproate and levetiracetam, and for the brain/plasma ratio. The statistical analysis was performed using the statistical software STATGRAPHICS (5.1 version). Statistical differences between the control groups (levetiracetam or sodium valproate alone) and the test group were evaluated using the student's t-test. The normality of the distribution and the homoscedasticity were checked before using a parametric method. If it was not applicable, the Mann-Whithney U-test was used.

Levetiracetam plasma concentrations in sub-studies were approximately 4.3 $\mu$g/ml. Concentrations were not different when given alone or in combination with valproate. Brain concentrations were about 50% of plasma concentrations. The brain/plasma ratio of levetiracetam was not modified when given in combination with valproate, that indicated the distribution profile (i.e. brain penetration) of levetiracetam was not change in the presence of valproate.

A 33% decrease of plasma concentrations (statistically significant) were obtained for valproate administered in combination with levetiracetam (table xx14). However, the brain/plasma ratio of valproate was not modified. It means, that the penetration of valproate was not modified by the coadministration of levetiracetamn.

TABLE xx14

|  | Plasma ($\mu$g/ml) | brain ($\mu$g/g) | brain/plasma ratio |
|---|---|---|---|
| Valproate 166.2 mg/kg alone | 222.5 ± 44.7 | 29.1 ± 8.2 | 0.13 ± 0.02 |
| Valproate 166.2 mg/kg + levetiracetam 5.4 mg/kg | 149.3 ± 32.4 | 21.1 ± 6.6 | 0.14 ± 0.03 |

Similar experiments were performed in order to evaluate a possible pharmacokinetic interaction between levetiracetam and other GABAergic agents, namely diazepam and phenobarbital.

Levetiracetam plasma concentrations were not different when given alone or in combination with phenobarbital. A 22% increase in plasma concentrations was obtained for levetiracetam administered in combination with diazepam. However, as for phenobarbital and valproate, the brain/plasma ratio of levetiracetam was not modified when given in combination with diazepam. This indicated that the distribution profile of levetiracetam was not changed in the presence of these compounds. Moreover, the plasma concentrations and brain/plasm ratio of diazepam and phenobarbital were unchanged when administered alone or in combination with levetiracetam, indicating that the distribution profile of these compounds was not modified in the presence of levetiracetam.

What is claimed is:

1. A method for treatment of bipolar disorders, mania, migraine or chronic or neuropathic pain comprising administering to a mammal in need thereof a therapeutically effective amount of levetiracetam.

2. The method according to claim 1 wherein bipolar disorder is treated.

3. The method according to claim 1 wherein mania is treated.

4. The method according to claim 1 wherein chronic pain is treated.

5. The method according to claim 1 wherein neuropathic pain is treated.

* * * * *